(12) United States Patent
Jesenko et al.

(10) Patent No.: US 9,468,508 B2
(45) Date of Patent: Oct. 18, 2016

(54) METHOD FOR OPTICAL ACQUISITION OF THE THREE-DIMENSIONAL GEOMETRY OF OBJECTS

(71) Applicant: a.tron3d GmbH, Klagenfurt am Worthersee (AT)

(72) Inventors: Jurgen Jesenko, Finkenstein (AT); Helmut Angerer, Klagenfurt (AT); Horst Koinig, Klagenfurt (AT)

(73) Assignee: A.TRON3D GMBH, Klagenfurt am Worthersee (AT)

( * ) Notice: Subject to any disclaimer, the term of this patent is extended or adjusted under 35 U.S.C. 154(b) by 295 days.

(21) Appl. No.: 14/200,640

(22) Filed: Mar. 7, 2014

(65) Prior Publication Data

US 2014/0255878 A1    Sep. 11, 2014

(30) Foreign Application Priority Data

Mar. 7, 2013  (DE) .................. 10 2013 102 279

(51) Int. Cl.
| | | |
|---|---|---|
| *G06T 17/10* | (2006.01) | |
| *A61C 9/00* | (2006.01) | |
| *A61B 5/00* | (2006.01) | |
| *G01B 11/25* | (2006.01) | |
| *G06T 1/00* | (2006.01) | |
| *A61B 5/107* | (2006.01) | |

(52) U.S. Cl.
CPC ........... *A61C 9/0053* (2013.01); *A61B 5/0062* (2013.01); *A61B 5/1077* (2013.01); *A61B 5/4547* (2013.01); *G01B 11/2518* (2013.01); *G06T 1/0007* (2013.01); *A61B 5/682* (2013.01)

(58) Field of Classification Search
None
See application file for complete search history.

(56) References Cited

U.S. PATENT DOCUMENTS 6,990,228 B1 *  1/2006  Wiles ...................... G06T 17/10
                                                                345/419

FOREIGN PATENT DOCUMENTS

| WO | 2007084647 A2 | 7/2007 |
| WO | 2012030357 A1 | 3/2012 |
| WO | 2012/115 862 | 8/2012 |
| WO | 2013/010 910 | 1/2013 |

OTHER PUBLICATIONS

European Search Report, dated Jul. 7, 2014, from corresponding EP application.
German Office Action dated Nov. 13, 2013, corresponding to the Priority Application No. 10 2013 102 279.0.

* cited by examiner

*Primary Examiner* — Kate Luo
*Assistant Examiner* — Janese Duley
(74) *Attorney, Agent, or Firm* — Young & Thompson

(57) ABSTRACT

In the case of a method for optical acquisition of the three-dimensional geometry of objects, in particular teeth (4), with a scanner (14), which has a scanning head (13), the three-dimensional geometry that is acquired in a virtual three-dimensional space (1) in the course of scanning is noted. In this case, in the course of scanning, positions of a defined scanner geometry (2) of the scanner (14), in particular of the scanning head (13), are noted relative to the object (4) that is acquired, and, moreover, an area (6) in which the defined scanner geometry (2) is or was located is determined. The determined area (6) is marked, for example as "empty," in the virtual space (1).

19 Claims, 3 Drawing Sheets

METHOD FOR OPTICAL ACQUISITION OF THE THREE-DIMENSIONAL GEOMETRY OF OBJECTS

FIELD OF THE INVENTION

The invention relates to a method for optical acquisition of the three-dimensional geometry of objects, in particular teeth, with a scanner, which has a scanning head, whereby in the course of scanning, the three-dimensional geometry that is acquired in a virtual three-dimensional space is noted.

BACKGROUND OF THE INVENTION

In particular in the area of dental treatments, many systems for optical acquisition of the three-dimensional geometry of objects are known. The latter are used, for example, in the creation of prostheses, crowns, fillings, or the like, are used to support the monitoring of orthodontic treatments, and/or are used to assist quite generally in the observation or acquisition of intraoral structures. The great advantage of such optical systems lies, on the one hand, in that they are neither invasive nor unpleasant as is the case of, for example, the dental impression frequently used in conventional dentistry and in that they also do not pose any potential danger to the patient, as is the case, for example, in radiation-based methods, such as X-rays. On the other hand, after the acquisition, the data are present in electronic form and can be easily stored, for example for later comparisons, or else can be forwarded, for example, from a dentist to a dentistry laboratory.

One problem that always arises in the optical method for acquisition of the three-dimensional geometry of objects, in particular teeth, is that soft parts that are present in the oral space, such as the insides of the cheeks or the tongue, are unintentionally acquired. It is usually difficult to correct such erroneous images after the fact, since even in the systems that provide several images of the same area, the erroneous images affect the geometry that is acquired or calculated and falsify the latter. Systems that join many individual areas to one another ("stitching") can overcome such erroneous measurements even less well since frequently no link can be found between individual areas. The object of the invention is therefore to make available a method that lessens this problem.

SUMMARY OF THE INVENTION

This object is achieved with a method of the above-mentioned type in that in the course of scanning, positions of a defined scanner geometry of the scanner, in particular of the scanning head, are noted relative to the object that is acquired, in that, moreover, an area in which the defined scanner geometry is or was located is determined, and in that the determined area is marked, for example as "empty," in the virtual space.

The underlying principle of the invention is based on—simply stated—the fact that where the scanner is or was located, there can be no solid object such as a tooth or, for example, even an implant.

This applies in particular when in one area in which the scanner is or was located, even surface data are noted. This occurs primarily in such surface data that were acquired from the tongue or the insides of the cheeks of a patient as described above. In this case, such falsely acquired surfaces are thus easily "rubbed" away by having the scanner be moved to the previous position of the tongue or having the patient's cheek be pressed to the side with the scanner or the scanning head and thus the corresponding scanner position be marked accordingly.

According to a preferred embodiment of the method, the latter represents a simple and especially intuitive handling for the operator so that when, in addition to the objects to be acquired, at least one movable obstructing object, for example a tongue, was acquired, the scanner is moved to the position of the obstructing object and possible data acquired by the obstructing object are marked, for example as "empty."

In this case, "empty" is defined only as a designation by way of example to ensure better understanding; "vacant," "free space," or the like or corresponding digital markings or data can also be noted. It is essential only that the determined area be marked and integrated so that none of the objects to be measured are located or can be located there, but rather only obstructing objects whose acquisition is not desired or whose acquisition represents a potential source of errors.

An additional great advantage of the invention, in addition to the intuitive application for operators, lies in the fact that areas once marked must no longer be part of subsequent calculations. After enough movements of the scanner or the scanning head, areas that are already large within the virtual space can be marked, and computer resources can be saved, which otherwise can be used, for example, for a faster calculation of a virtual model of the object that is acquired.

According to another preferred embodiment of the method, the scanner geometry of the scanner, in particular of the scanning head, is defined before acquisition of the three-dimensional geometry of the objects, and the scanner geometry is the same size as or smaller than the scanner or scanning head. This representative or defined scanner geometry then reproduces in the virtual space the movements of the real scanner or scanning head. Configuring the defined scanner geometry smaller than the actual scanner in this case has two advantages or causes. On the one hand, large portions of the scanner handpiece protrude from the oral space and are not relevant to the acquisition or would require room in the virtual space and thus would possibly negatively affect its overall size. On the other hand, the actual shape of the scanner is usually selected according to ergonomic and optical aspects and can therefore have many curves and shapes that are unnecessarily complicated from the computer standpoint. Of course, the exact shape of the scanner can also be defined as scanner geometry. However, even a simplified shape, for example a cuboid that lies within the actual shape of the scanner or scanning head, is sufficient for the method and even advantageous with respect to the required processing power.

According to another preferred embodiment of the method, the virtual space is an $n^3$-voxel grid. This special type of notation has proven to be especially suitable for the notation of the three-dimensional geometries that are acquired. According to a preferred further development of the invention, it thus is possible to mark entire voxels of the $n^3$-voxel grid.

In a further development of the invention, the marking can be cancelled by an input. In an additional or alternative embodiment of the invention, marked areas can also be set back completely or partially by an input. This can be advantageous, for example, when the scanner has been located in an area in which a prosthesis is inserted. In the case of systems that make possible the continuation of the optical acquisition after changes (for example preparations or the insertion of prostheses) based on the original image, areas marked as "empty," in which surfaces to be acquired in the reimaging are located, would otherwise be acquired falsely or not at all.

According to another preferred embodiment of the invention, areas that lie on the side of the scanner geometry, which is facing away from the acquired geometry, are also marked. This embodiment is comparable to an embodiment in which the defined scanner geometry projects over the rear side of the real scanning head. The advantage of this embodiment is that the proportion of the areas that are no longer part of the calculation of the surface and thus do not tie up the computer resources is increased without the scanner actually having to be at any of these spots. In this case, however, it is disadvantageous that if, for example, the inner side of a jaw arch is acquired, areas that are actually to be acquired can also be marked, such as, for example, a jaw arch opposite the inner side. According to an advantageous further development, this additional marking can also be turned on and off during a continuous imaging.

According to another additional or alternative embodiment of the invention, marked areas are combined into area groups. For example, in the case of an $n^3$-voxel grid, voxels can be combined into groups of 8, 64 and 512 and the like similar to a bottom-up octree. In the case of an octree, for example, the marking can be carried out on higher octree levels and requires correspondingly less memory space.

In general, the marking of areas can be used not only for the protection of computer resources but rather also for improved memory allocation.

Accordingly, in a further development of the invention and in systems that make possible the continuation of the optical acquisition based on the original image, the finding of correspondence, i.e., the determination of the point at which the acquisition is to be continued, can be facilitated. On the one hand, marked areas or area groups can be bypassed in the search for correspondence, which saves considerable computer time; on the other hand, the marked areas themselves can be a criterion for finding correspondence. This means that correspondences are to be considered to be valid only when not only the determined surface is identical to the correspondence-surface (within specific tolerances) but also the scanner is located, optionally completely, in a marked area.

Other preferred and advantageous embodiments of the method according to the invention are the subject matter of the other subclaims.

BRIEF DESCRIPTION OF THE DRAWINGS

An application of the method according to the invention, only by way of example, is explained in more detail below based on the drawings. The latter are shown in greatly simplified form.

DETAILED DESCRIPTION OF THE INVENTION

A virtual space for noting optically acquired surface geometries is usually three-dimensional, and it provides a number of different notation methods for the acquired surface geometry within the virtual space. The depicted example shows a preferred embodiment of the invention, in which the surface geometry is noted in an $n^3$-voxel grid. This depiction is defined only by way of example and is not limiting. The essential features of the invention can also apply to other forms of the notation. To ensure better understanding, only a small portion of the voxel grid is pictured. In this case, the voxel grid itself is depicted very much larger than it is in reality. Also, only two dimensions are shown for the sake of simplicity. Applications of the invention, for example in the implantology in which the virtual space is two-dimensional, are also conceivable.

Figure 1:
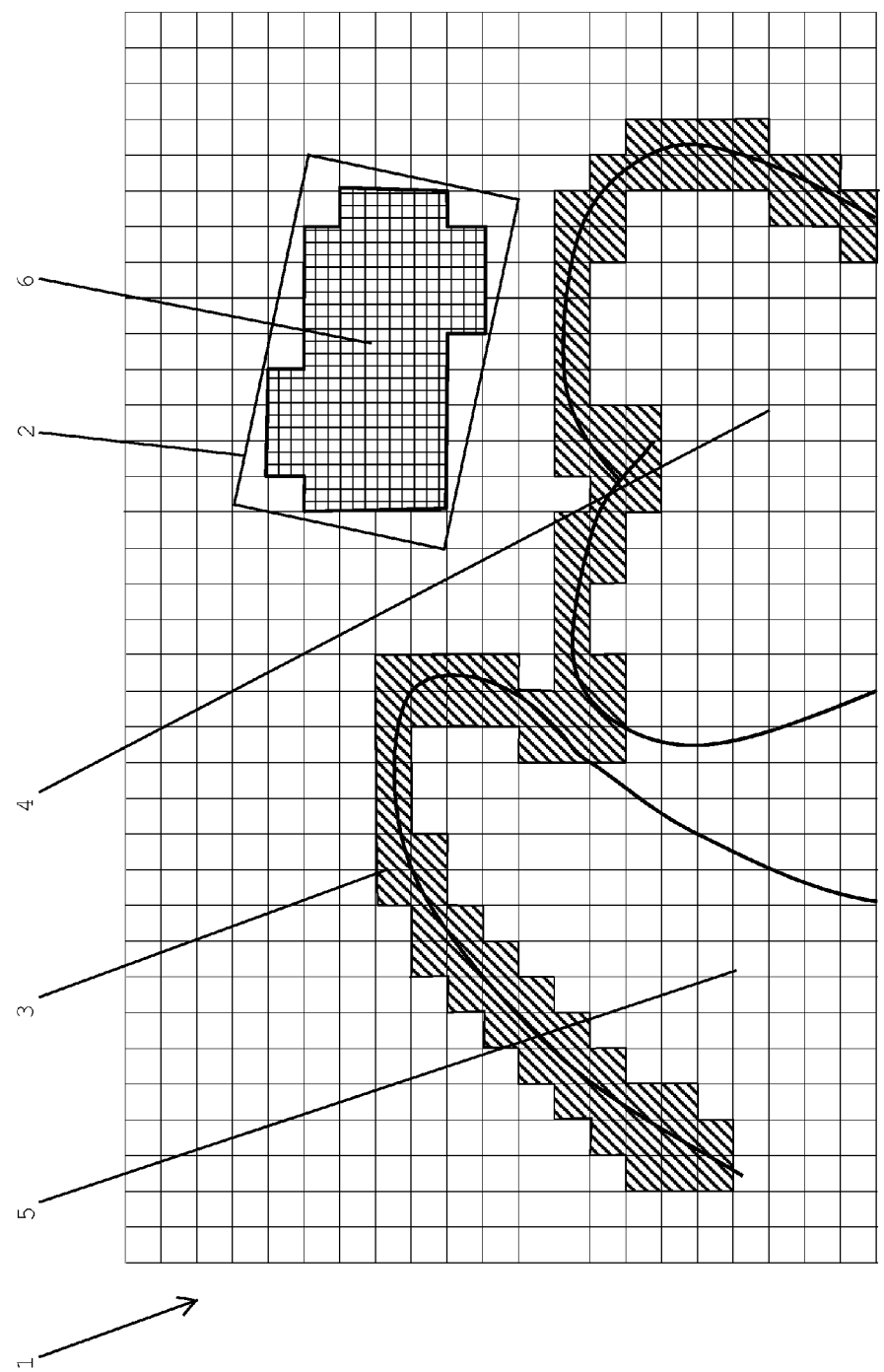
FIG. 1 Two dimensions of a voxel grid with a scanner geometry, and an erroneously acquired surface of a symbolically depicted tooth and a tongue, FIG. 2 The voxel grid of FIG. 1 with a marked area, and FIG. 3 A diagrammatic sketch for acquiring a position of a scanner geometry.

FIG. 1 shows two dimensions of a voxel grid 1 with a defined scanner geometry 2 and an erroneously acquired surface 3 of a symbolically depicted tooth 4 and a tongue 5. An area 6 is marked within the scanner geometry 2. In this case, this area 6 comprises only complete voxels, in which the scanner geometry is located. In alternative types of notations, of course, the entire area in which the scanner is located can also be noted. Also, it is even possible to mark voxels that only partially contain the scanner geometry. The selection of the notation of the area can be made freely by one skilled in the art and according to the type thereof for optical acquisition of the surface geometry.

The scanner geometry is now moved through the virtual space, i.e., through the voxel grid in the depicted example. The necessary positional data of the real scanner in this case can be obtained essentially in two types. On the one hand, its position, for example relative to the earth's magnetic field, can be acquired via a sensor in the scanner. This method is unreliable, however, since the object can also move and thus the scanner can occupy a position in which an actual object that is to be measured was located earlier. In contrast, it is much more reliable to acquire the position of the scanner or the scanning head in the course of the optical acquisition of the surface geometry. In this case, the position of the scanner or scanning head is noted relative to the acquired surface.

Figure 3:
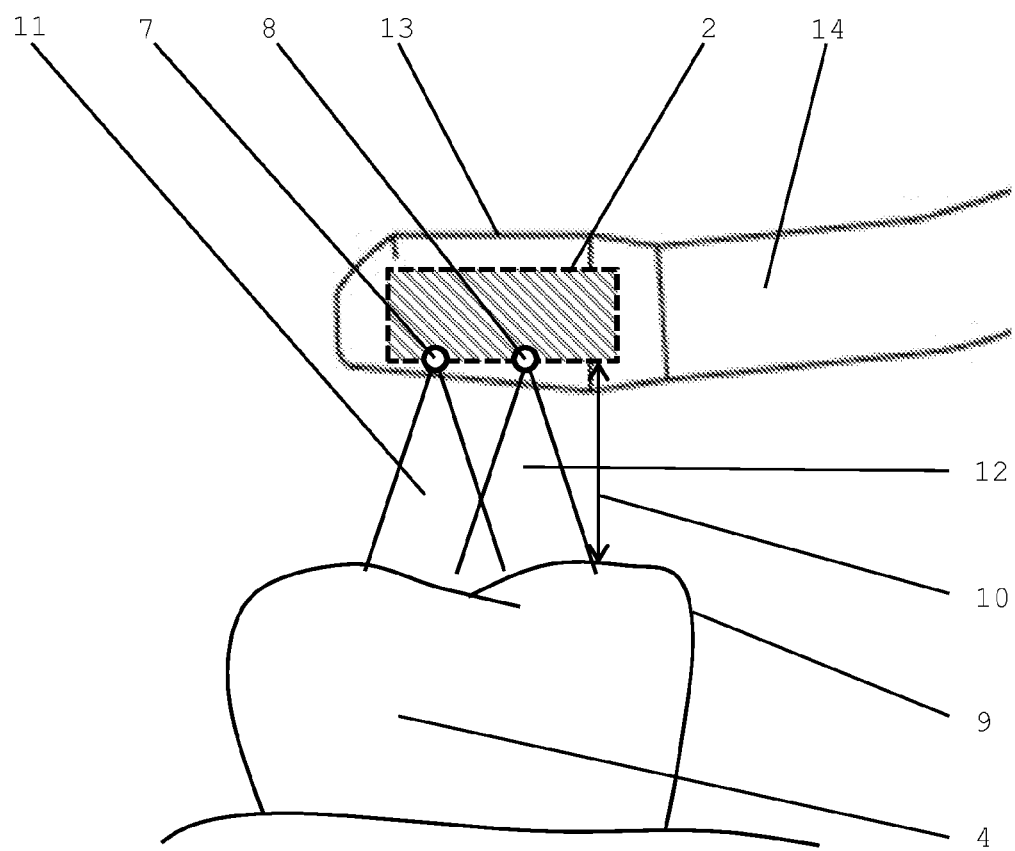

The principle underlying this notation is outlined in FIG. 3. All methods for optical acquisition of surface geometries have in common that a triangulation between two instruments 7, 8 and the real surface 9 is performed. In this case, the instruments 7, 8 can be a projector and a sensor, depending on the system, or two sensors. This can be carried out by two images of a sensor from various known positions or by two sensors with a known spatial ratio to one another. In the latter case, these are stereometric methods, as they are used according to a preferred embodiment of the invention. Usually, a distance (shown by an arrow 10) is determined between the instruments 7, 8 and the surface 9 by triangulation. The instruments 7, 8 usually have cone-shaped imaging and/or projection areas 11, 12. In the depicted example, for a simpler explanation, the instruments 7, 8 are arranged directly in a scanning head 13. In reality, the instruments 7, 8 are usually located at other sites inside or else outside the scanner, and the projection or imaging is done using mirrors, optical conductors, and the like.

In this case, the cone-shaped areas represent the imaging and/or projection areas of optics of, for example, cameras or projectors. Systems with more sensors or projectors are also known. The invention can also be applied to such systems.

In addition, FIG. 3 shows a scanner geometry 2 that is defined by way of example and that is arranged within the scanning head 13. In the virtual space, the latter is positioned in the depicted example in each image at the determined distance from the acquired (virtual) surface. In the case of other arrangements and imaging methods, the position can be selected by one skilled in the art relative to the acquired surface corresponding to the scanner design. The dimensions of the defined scanner geometry 2 are selected considerably smaller in the depicted example than the dimensions of the real scanning head 13. Thus, i.a., the possibility that the measuring errors will result in a "rubbing-out" of desired surface data is avoided.

Figure 2:
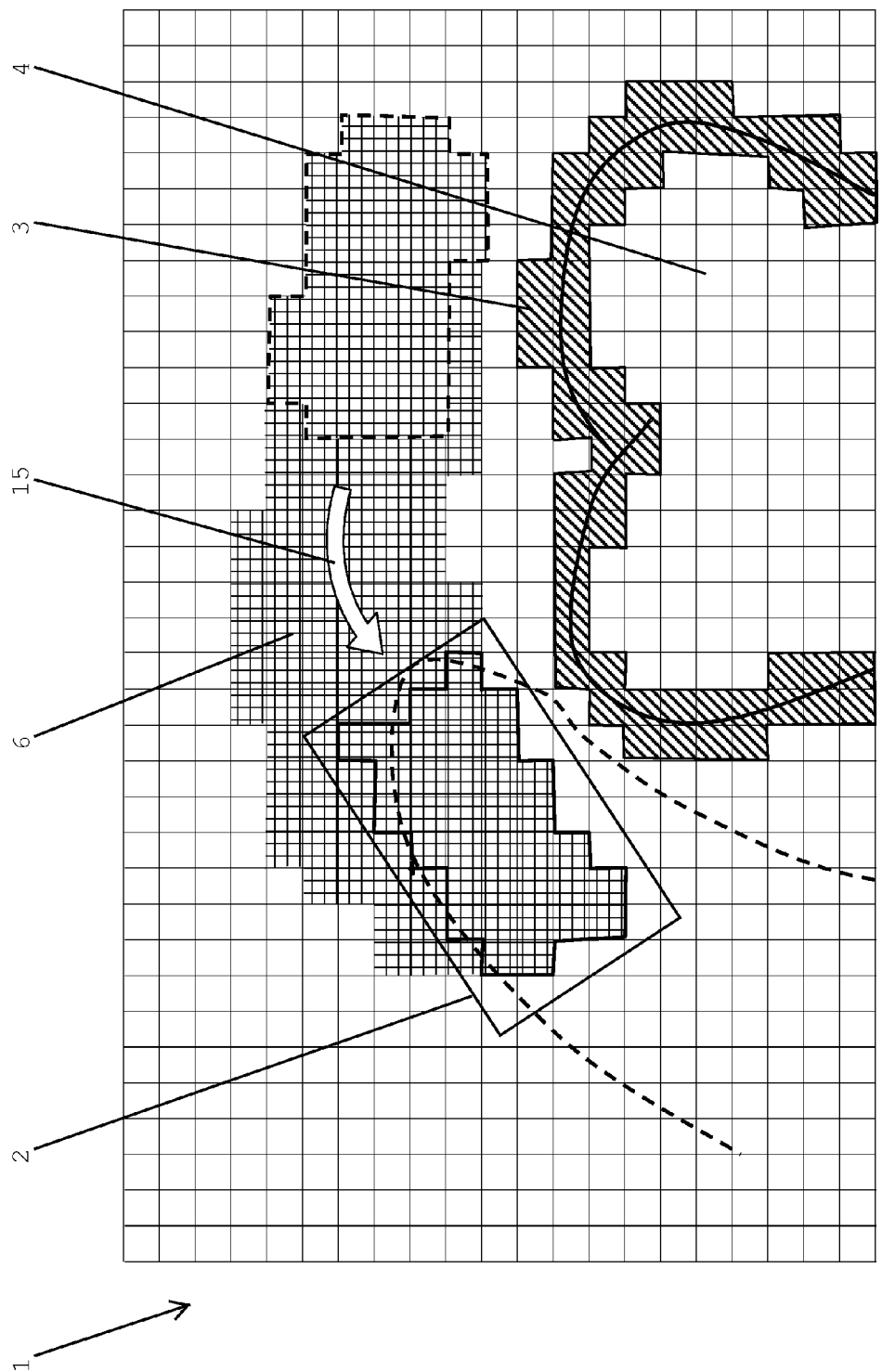

FIG. 2 shows the voxel grid of FIG. 1 with a marked area. In this case, the scanner geometry 2 is moved through the virtual space as indicated by an arrow 15. The area 6 is enlarged here with the voxels marked as "empty." The surface acquired in FIG. 1 of the obstructing object, i.e., the tongue 5, is transcribed or marked by the scanner geometry 2 and is no longer part of the calculations of the surface geometry.

The invention claimed is:

1. A method for optical acquisition of a three-dimensional geometry of objects with a scanner (14) that includes a scanning head (13), whereby the three-dimensional geometry that is acquired in a virtual three-dimensional space (1) in the course of scanning is noted,
wherein in the course of scanning, positions of a defined scanner geometry (2) of the scanning head (13) of the scanner (14) are noted relative to the object (4) that is acquired,
wherein an area (6) in which the defined scanner geometry (2) is or was located is determined,
wherein the determined area (6) is marked in the virtual space (1),
wherein the scanner geometry (2) of the scanning head (13) of the scanner (14) is defined before acquisition, and
wherein the scanner geometry (2) is a same size or smaller than the scanner (14) or scanning head (13).

2. The method according to claim 1, wherein when, in addition to the objects (4) to be acquired, at least one movable obstructing object was acquired, the scanner (14) is moved to the position of the obstructing object (5) and wherein possible data acquired from the obstructing object (5) are marked.

3. The method according to claim 1, wherein the acquisition is done stereometrically.

4. The method according to claim 1, wherein the virtual three-dimensional space (1) is an n3-voxel grid.

5. The method according to claim 4, wherein voxels of the n3-voxel grid are marked when they at least partially contain the determined area (6).

6. The method according to claim 1, wherein the marking is cancelled by an input.

7. The method according to claim 1, wherein the marked areas are set back.

8. The method according to claim 4, wherein voxels are set back.

9. The method according to claim 1, wherein areas that lie on the side of the scanner geometry (2), which is facing away from the acquired geometry (3), are also marked.

10. The method according to claim 1, wherein marked areas are combined into area groups.

11. The method according to claim 2, wherein the acquisition is done stereometrically.

12. The method according to claim 2, wherein the virtual three-dimensional space (1) is an n3-voxel grid.

13. The method according to claim 3, wherein the virtual three-dimensional space (1) is an n3-voxel grid.

14. The method according to claim 2, wherein the marking is cancelled by an input.

15. The method according to claim 4, wherein the marking is cancelled by an input.

16. The method according to claim 1, wherein the determined area (6) is marked as "empty," in the virtual space (1).

17. The method according to claim 2, wherein the at least one movable obstructing object is a tongue (5).

18. The method according to claim 2, wherein possible data acquired from the obstructing object (5) are marked as "empty".

19. The method according to claim 5, wherein voxels of the n3-voxel grid are marked as "empty" when they at least partially contain the determined area (6).

* * * * *